United States Patent
Varadi et al.

(10) Patent No.: US 8,735,086 B2
(45) Date of Patent: May 27, 2014

(54) KIT FOR MEASURING THE THROMBIN GENERATION IN A SAMPLE OF A PATIENT'S BLOOD OR PLASMA

(75) Inventors: Katalin Varadi, Vienna (AT); Peter Turecek, Klosterneuburg (AT); Brigitte Keil, Vienna (AT); Sylvia Peyrer-Heimstaett, Vienna (AT); Hans-Peter Schwarz, Vienna (AT)

(73) Assignees: Baxter International Inc., Dearfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 13/539,154

(22) Filed: Jun. 29, 2012

(65) Prior Publication Data

US 2013/0052672 A1    Feb. 28, 2013

Related U.S. Application Data

(63) Continuation of application No. 10/816,099, filed on Mar. 31, 2004, now abandoned.

(51) Int. Cl.
*C12Q 1/56*    (2006.01)

(52) U.S. Cl.
USPC .......................................................... 435/13

(58) Field of Classification Search
USPC .......................................................... 435/13
See application file for complete search history.

(56) References Cited

U.S. PATENT DOCUMENTS

| | | | |
|---|---|---|---|
| 5,059,525 A | 10/1991 | Bartl et al. | |
| 5,314,695 A | 5/1994 | Brown | |
| 5,418,141 A | 5/1995 | Zweig et al. | |
| 5,529,905 A | 6/1996 | Lang et al. | |
| 5,625,036 A | 4/1997 | Hawkins et al. | |
| 5,952,198 A | 9/1999 | Chan | |
| 6,074,826 A | 6/2000 | Hogan et al. | |
| 6,124,110 A | 9/2000 | Wöber et al. | |
| 6,387,881 B1 | 5/2002 | Kakkar et al. | |
| 6,576,422 B1 | 6/2003 | Weinstein et al. | |
| 6,756,019 B1 | 6/2004 | Dubrow et al. | |
| 2002/0151582 A1 | 10/2002 | Dou et al. | |

FOREIGN PATENT DOCUMENTS

| | | |
|---|---|---|
| WO | WO 92/08479 A1 | 5/1992 |
| WO | WO 93/07492 A1 | 4/1993 |
| WO | WO 95/30770 A1 | 11/1995 |
| WO | WO 98/48283 A1 | 10/1998 |
| WO | WO 03/001964 A2 | 1/2003 |

OTHER PUBLICATIONS

Lawson et al.; "The evaluation of complex-dependent alterations in human Factor VIIa";*J. Biol. Chem.*; 267(7):4834-4843 (1992).

(Continued)

*Primary Examiner* — Rosanne Kosson
(74) *Attorney, Agent, or Firm* — Kilpatrick Townsend & Stockton LLP

(57) ABSTRACT

The invention provides a kit for measuring the thrombin generation in a sample of a patient's blood or plasma, or in a sample of clotting factors. The kit contains lyophilized tissue factor/phospholipid-complex and a lyophilized mixture containing a thrombin-substrate and $CaCl_2$. The invention also provides processes for preparing the reagents for the kit. The kit can be used in a method for measuring the thrombin generation in a sample, wherein it is possible to detect changes in thrombin generation kinetics, for example after administration of inhibitor bypassing agents to a patient who has developed inhibitors to an exogenous clotting factor such as Factor VIII.

10 Claims, 5 Drawing Sheets

(56) References Cited

OTHER PUBLICATIONS

Turecek et al. ; "Factor VIII Inhibitor-Bypassing Agents Acts by Inducing Thrombin Generation and Can Be Monitored by a Thrombin Generation Assay"; *Pathophysiology of Haemostasis and Thrombosis;* 33: 16-22 (2003).

Váradi et al.; "Monitoring the bioavailability of FEIBA with a thrombin generation assay," *J. Thrombosis and Heamostasis*; 1:2374-2380 (2003).

*CRC Handbook of Chemistry and Physics.* 51st Ed., R.C. Weast, ed., The Chemical Rubber Co., Cleveland, 1970, p. B-77.

KIT FOR MEASURING THE THROMBIN GENERATION IN A SAMPLE OF A PATIENT'S BLOOD OR PLASMA

CROSS-REFERENCE TO RELATED APPLICATIONS

This application is a continuation of U.S. patent application Ser. No. 10/816,099, filed Mar. 31, 2004, the contents of which are herein incorporated by reference.

FIELD OF INVENTION

The present invention relates to a kit for measuring the thrombin generation in a sample of a patient's blood or plasma, or in a sample of clotting factors. The invention also relates to processes for preparing reagents for the kit.

BACKGROUND OF THE INVENTION

Haemophilia A is a hereditary blood coagulation (clotting) disorder. It is caused by a deficient activity of the plasma protein factor VIII, which affects the clotting property of blood. The standard treatment for Haemophilia A patients is the infusion of factor VIII concentrates to replace the defective clotting factor. However, Haemophilia A patients who develop inhibitors to factor VIII during replacement therapy consequently fail to respond to the above-mentioned therapy and are treated with preparations containing activated coagulation factors (so-called bypassing agents) to achieve haemostasis independently of factor VIII through bypassing mechanisms. Both activated prothrombin complex concentrates (APCC) such as FEIBA (Factor Eight Inhibitor Bypassing Activity—plasma-derived APCC), which triggers the intrinsic or common pathway, and activated factor VIIa (rFVIIa) such as NovoSeven (recombinant FVIIa), which is assumed to act via the extrinsic pathway, are favoured options to treat factor VIII inhibitor patients.

No direct monitoring of the drug substance is possible for either treatment regime because the activated components of the bypassing agents interact immediately with proteins of the haemostatic system to induce activation of the clotting cascade. All existing assays measure surrogate markers, which are of limited value for the assessment of the efficacy of the bypassing agent because the specificity and sensitivity depend on the specific assay conditions and because these assays do not give any information on the overall activity status of the haemostatic system.

The ultimate goal of the coagulation cascade is the conversion of prothrombin into thrombin, which then induces clot-formation by activation of fibrinogen. Thus, generation of thrombin is a pivotal function of plasma in haemostasis. Currently there is no routine test that quantitatively assesses the thrombin formation capacity of a plasma sample. Clotting times such as prothrombin time (PTT), activated partial thromboplastin time (aPTT) and thrombin clotting time (TCT) do not reflect the overall thrombin generation because most of the thrombin is formed after the instant of clotting and, therefore, they are insensitive to hypercoagulation and possibly also to hypocoagulation states. The PTT-test measures the clotting time of the extrinsic and common pathway, the aPTT-test measures the clotting time of the intrinsic and common pathway, whereas the TCT-test only measures the clotting time of the common pathway. Hemker et al. (1986. Thromb. Haemost. 56:9-17) were the first to suggest measurement of thrombin generation in patient plasma by assessment of the endogenous thrombin potential. Thrombin generation is a dynamic process. The actual thrombin concentration is dependent on the rate of the activation and inactivation reactions, and thus, reflecting the efficiency of the haemostatic system to control bleeding. Hemker et al. (1995. Thromb. Haemost. 74:134-138) defined the thrombin potential as the overall capacity of plasma to form thrombin after induction of coagulation and proposed the use of this parameter as a sensitive indicator of every form of anticoagulation.

Sultan and Loyer (1993. J. Lab. Clin. Med. 121:444-452) used such a thrombin generation assay for in vitro evaluation of the factor VIII-bypassing activity of activated prothrombin complex concentrates, prothrombin complex concentrates and factor VIIa in the plasma of patients with factor VIII inhibitors. There have also been other reports of such assays being used for assessing the efficacy of factor VIII-bypassing agents but, because of their technical complexity, the assays have not disseminated into routine use.

Thrombin generation assays were also described by Turecek at al. (2003. Pathophysiol. Haemost. Thromb. 33:16-22), however, no lyophilized components were used. Moreover, there is the common opinion that lyophilization decreases the activity of the tissue factor.

All the known prior art assays have the disadvantage that components can only be partially dosed before using the assay. Therefore, a lot of preparation steps are necessary to use these assays thereby making the assays uncomfortable and susceptible to mistakes during handling. Moreover, these assays are time-consuming.

It therefore exists a need for a test system which allows the detection and determination of changes, e.g. treatment-dependent changes, in the kinetic of thrombin generation in a sample of a patient's blood or plasma which overcomes the above-mentioned problems.

SUMMARY OF THE INVENTION

An object of the present invention is to provide a kit for measuring the thrombin generation in a sample of a patient's blood or plasma, or in a sample of clotting factors. The kit comprises a lyophilized tissue factor (TF)/phospholipid (PL)-complex and a lyophilized mixture containing a thrombin-substrate and $CaCl_2$. Additionally, the kit of the present invention may also contain any auxiliary agents, such as buffers, salts, e.g. $CaCl_2$, thrombin standards, FEIBA standards etc., in frozen or in lyophilized form. The kit of the present invention may be present in any shape, e.g. immobilized on a support.

Surprisingly, it has been found that a lyophilized TF/PL-complex and a lyophilized mixture containing a thrombin-substrate and $CaCl_2$ provide a simple, efficient, fast and reproducible assay system for measuring the thrombin generation in a sample. The kit of the present invention provides at least a lyophilized TF/PL-complex and a lyophilized mixture containing a thrombin-substrate and $CaCl_2$ in easy resolvable lyophilized form, whereby only the addition of a sample to be tested is necessary. The lyophilized TF/PL-complex and said lyophilized mixture containing a thrombin-substrate and $CaCl_2$ of the claimed kit can also be immobilized onto a support, such as the inner surface of a vial or the well of a microtiter-plate, whereby the thrombin generation assay is brought to an assay format known from conventional ELISAs, thus, making it a very convenient type of assay. The kit of the present invention provides at least the same sensitivity in the thrombin generation assay than prior art assays using frozen components. Therefore, the thrombin generation assay performed with the kit of the present invention allows a rapid diagnosis of the overall activity status of the haemostatic system of a patient. Further, it is possible to detect treatment-dependent changes in the thrombin generation kinetics, for example after administration of bypassing therapeutics to a patient, whereby it is possible to optimize the treatment intervals and doses of therapeutics helping to avoid thrombotic complications due to overdosing.

DETAILED DESCRIPTION OF THE INVENTION

Figure 1:
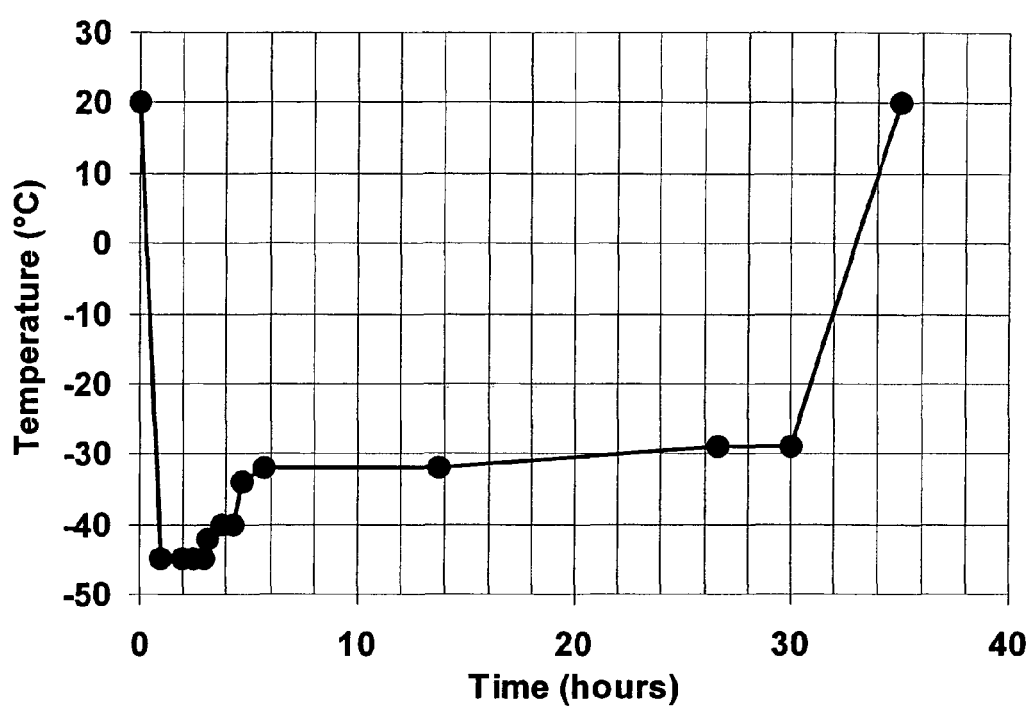
FIG. 1 shows the changes of temperature during the lyophilization cycle of the TF/PL-complex. The long lasting lyophilization cycle with small gradient temperature changes during the main drying period and the slow warming up period up to a maximum of low room temperature of 20° C. preserves the biological activity of the TF/PL-complex.

One embodiment of the invention is a kit for measuring the thrombin generation in a sample comprising a lyophilized tissue factor (TF)/phospholipid (PL)-complex and a lyophilized mixture containing a thrombin-substrate and $CaCl_2$.

The term "sample" as used herein refers to a biological fluid such as whole blood or plasma, e.g. blood-cell-enriched plasma or cell-free plasma, of humans or animals. The sample may be obtained from healthy individuals or from individuals suspected to have or having a blood coagulation disorder in particular a disorder associated with the occurrence of FVIII inhibitors without or under treatment. The sample can be freshly prepared or be present in frozen condition, e.g. in case of the cell-free samples. The sample can also consist of mixtures of purified proteins of natural, synthesized or recombinant origin and/or other preparations/reagents with haemostatic activity.

The weight ratio of TF and PL in the lyophilized TF/PL-complex is variable depending on the purpose. For the thrombin generation assay, in general, a low amount of TF and a low amount of PL is preferred. In a preferred embodiment of the present invention the concentration of TF in the TF/PL-complex ranges from about 5 to about 1000 pM and/or the concentration of PL in the TF/PL-complex ranges from about 1 to about 100 µM.

The TF in the TF/PL-complex is either a full-length tissue factor or at least a functional part thereof. The tissue factor could be of natural or recombinant origin. The expression "at least a functional part thereof" means every part of the tissue factor that exhibits the same function as the full-length tissue factor. In a preferred embodiment a human full-length recombinant tissue factor is used.

The PL of the TF/PL-complex may be of synthetic or natural origin. The composition of the PL vesicles depends on their coagulation relevance, i.e. their role in the physiological blood coagulation. In a preferred embodiment of the present invention the phospholipids are selected from the group consisting of phosphatidylserine (PS), phosphatidylcholine (PC), phosphatidylethanolamine (PE) and mixtures thereof. Preferably, the phospholipids are selected from the group of 1,2-Dioleyl-sn-glycero-3-phosphocholine (DOPC), 1-Palmitoyl-2-oleyl-sn-glycero-3-phosphoserine (POPS) and 1,2-Dioleyl-sn-glycero-3-phosphoethanolamine (DOPE). In a preferred embodiment of the present invention the weight ratio of PC/PS is in the range of from about 60/40 to about 95/5, based on the total amount of phospholipids, and the weight ratio of PC/PS/PE is in the range of from about 60/20/20 to about 78/17/5 based on the total amount of phospholipids.

The TF/PL-complex as well as the mixture containing a thrombin-substrate and $CaCl_2$ can be immobilized on a support individually or jointly. The term "immobilized" encompasses either an immobilization onto a support simply by lyophilization or by an interaction or coupling, such as a covalent coupling directly or via a linker molecule, with the support. Preferably, the lyophilized TF/PL-complex and the lyophilized mixture containing a thrombin-substrate and $CaCl_2$ are lyophilized jointly to a support. The immobilization is performed in such a way that the biological activity of the components, e.g. TF, PL and thrombin-substrate, is substantially maintained. The term "support" does not exhibit any specific limitations, and relates for example to the surface of an inert material such as a polymer material which can be an organic polymer, such as polyamide or a vinyl polymer (e.g. poly(meth)acrylate, polystyrene and polyvinyl alcohol, or derivates thereof) or a natural polymer such as cellulose, dextrane, agarose, chitin and polyamino acids, or an inorganic material, such as glass. The support can be in any shape and form such as the inner surface and the bottom of vials, microcarrier, particles, membranes, strips, papers, film, pearls or plates, such as microtiter plates having wells.

The thrombin-substrates used in the present invention are known in the art and should preferably be highly specific for thrombin, i.e. there are substantially no or negligible cross-reactions with other coagulation enzymes, and should have preferably a low affinity to thrombin (high Km) to enable a long-time kinetic. The thrombin-substrate comprises a labeled moiety wherein the labeled moiety can be cleaved off by thrombin. The label of this moiety can be a fluorescent or radioactive label. In a preferred embodiment of the present invention the labeled moiety of the thrombin-substrate comprises a fluorophore. Moreover, the labeled moiety comprises preferably a peptide, such as a di- or tripeptide.

According to one embodiment of the invention the kit further comprises at least one thrombin standard as a reference.

The present invention also relates to a process for preparing a lyophilized TF/PL-complex, whereby it is possible to obtain highly active TF the activity of which is maintained during the lyophilization process.

The process for preparing the TF/PL-complex comprises the following steps:
  (a) preparing phospholipid vesicles having a diameter in the range of about 200 to about 300 nm preferably by any method known in the art such as extrusion or sonication;
  (b) lyophilizing the phospholipid vesicles to obtain a powder;
  (c) reconstituting the lyophilized powder with water for injection and mixing it with a tissue factor;
  (d) freezing and thawing the mixture obtained in step (c) to form a TF/PL-complex;
  (e) stabilizing the TF/PL-complex by incubating at about 4° C. for about 24 to 72 hours, and optionally diluting the TF/PL-complex to an appropriate "ready to use" concentration; and
  (f) lyophilizing the TF/PL-complex.

In the invention process for preparing the TF/PL-complex the addition of preservatives is not essential. The use of preservatives would make the preparation of an assay more time-consuming and expensive. Further, some of these preservatives, like albumin, are not suitable as it is known that albumin interacts with many proteins, thereby negatively affecting the assay.

In step (d) of the process the freezing and thawing cycle is preferably carried out by freezing the tissue factor with the phospholipid vesicles at about −20° C. overnight and then thawing for about 30 minutes at room temperature.

The present invention encompasses a process for preparing a mixture containing a thrombin-substrate and $CaCl_2$ resulting in an easily water-dissolvable preparation. The thrombin-substrate preparations known in the prior art require initial dissolution in a suitable buffer, often containing DMSO, followed by further dilution with water. The subsequent addition of $CaCl_2$ to prior art thrombin substrate preparations results in a precipitate which is difficult to dissolve and thus difficult to use.

The process for preparing the lyophilized mixture containing a thrombin-substrate and $CaCl_2$ comprises the following steps:
  (a) dissolving the thrombin-substrate in a suitable solvent;
  (b) adding $CaCl_2$ and dissolving the formed precipitate containing the thrombin-substrate and $CaCl_2$, particularly to get a clear solution; and
  (c) lyophilizing the mixture containing the thrombin-substrate and $CaCl_2$.

The dissolution in step (b) is preferably carried out at a temperature of about 37° C. until a clear solution appears.

Moreover, the present invention relates to a method for measuring the thrombin generation in a sample e.g. obtained from a patient, comprising the steps of:
  (a) providing a lyophilized TF/PL-complex and a lyophilized mixture containing thrombin-substrate as defined above and $CaCl_2$;
  (b) contacting the sample with said lyophilized TF/PL-complex and said lyophilized mixture containing thrombin-substrate and $CaCl_2$; and
  (c) measuring the thrombin generation in the sample.

When using the kit of the present invention, provided that a thrombin-substrate having a fluorescent labeled moiety is used, the development of the fluorescence intensity of the liberated fluorophore can be monitored continuously. The rate of development of fluorescence intensity (fluorescence units (FU)) is calculated for each reading (FU/min), and can be converted to thrombin equivalent concentrations (nM) using a reference curve prepared by measuring the rate of substrate conversion by a thrombin standard.

The kit and method of the present invention are highly sensitive for assaying one or more coagulation factors of the blood coagulation cascade via the thrombin generation. Accordingly, the kit and the method of the present invention can be used for monitoring any treatment affecting the haemostasis by increasing or decreasing the activity of any coagulation factor, e.g. monitoring of the treatment with FVIII bypassing agents or Vitamin K antagonists. Moreover, the monitoring of the treatment with therapeutics, such as bypassing therapeutics, will allow the optimization of treatment intervals and dosing of these therapeutics and will help to avoid thrombotic complications due to overdosing.

Further, the lyophilized reagents of the kit of the present invention have a higher expiry date and are more reproducible compared to an assay using frozen components. Moreover, no dilution steps are necessary by using the claimed assay kit making the handling of such an assay kit easier and more comfortable.

The present invention will be further illustrated in the following examples, without being limited thereto.

EXAMPLES

Example 1

Preparation of a Frozen and a Lyophilized TF/PL-Complex

A tissue factor having phospholipid vesicles (TF/PL-complex) is prepared by using a recombinant full-length TF (American Diagnostica Inc. Greenwich, Conn., USA) and synthetic PLs (Avanti Polar Lipids, Alabaster, Ala., USA). The preparation comprises the following steps:

Phospholipid vesicles composed of 1,2-Dioleyl-sn-glycero-3-phosphocholine (DOPC), 1-Palmitoyl-2-oleyl-sn-glycero-3-phosphoserine (POPS) and 1,2-Dioleoyl-sn-glycero-3-phosphoethanolamine (DOPE) (Avanti Polar Lipids, Alabaster, Ala.) are prepared by the extrusion method of Hope et al. (Hope M J, Bally M B, Webb G, Cullis PR: "Production of large unilamellar vesicles by a rapid extrusion procedure. Characterization of size distribution, trapped volume and ability to maintain a membrane potential." Biochim Biophys Acta 812:55, 1985) using an extrusion device of Lipex Biomembranes, Inc. (Vancouver, Canada) equipped with two stacked polycarbonate filters (pore size 1000 nm). The vesicle preparation is diluted with 20 mM TRIS buffer pH 7.4 containing 150 mM NaCl (TBS) to a concentration of 1.27 mM and freeze-dried after addition of 5% sucrose (w/v). After reconstitution of the freeze-dried powder with distilled water, the vesicles have a mean diameter of 260 nm as determined by dynamic light scattering (Zetasizer 4, Malvern Instruments, Worcestershire, UK).

Complexing of TF with the PL vesicles: A starting mixture of 2 to 700 nM TF with 850 μM PL vesicles is frozen at −20° C. overnight, then thawed for 30 minutes at room temperature and diluted 6.7-fold with TBS. The TF/PL vesicles are equilibrated at 4° C. for 48 to 168 hours, and are frozen in aliquots or lyophilized without or in the presence of 0.5 and 5% sucrose. As a second choice, they were diluted to 40 fold to give the appropriate working concentrations of 3.2 μM PL and various TF concentrations and are frozen in aliquots or lyophilized without or in the presence of 0.5 and 5% sucrose.

TABLE 1

| Core data of the lyophilization cycle | | | | | | | | |
|---|---|---|---|---|---|---|---|---|
| Freezing | | | | Main drying | | | Final drying | |
| Loading | Temperature | Duration | Pressure | Temperature | Duration | Pressure | Temperature | Duration |
| +20° C. | −45° C. | 2 h | 0.1 mbar | −45° C.→ −30° C. | 27 h | <0.03 mbar | up to 20° C. | 6 h |

FIG. 1 shows the changes of temperature during the lyophilization cycle.

Example 2

Thrombin Generation Triggered with Frozen or Lyophilized TF/PL-Complex in Various Plasma Samples The thrombin generation is triggered by a TF/PL-complex, prepared as described above containing 18 pM TF and 3.2 μM PL, wherein the PL is composed of a ratio of 80% by weight DOPC and 20% by weight POPS. The lyophilized TF/PL-complex is dissolved in water for injection (to a final concentration of 18 pM TF and 3.2 μM PL) and 10 μL of this aqueous solution is added to 50 μL of 1 mM thrombin substrate Z-Gly-Gly-Arg-AMC (Bachem AG, Bubendorf, Switzerland) premixed with 15 mM $CaCl_2$. For comparison 10 μL of a frozen TF/PL-complex (18 pM TF and 3.2 μM PL) is mixed with 50 μL of the above mentioned thrombin-substrate. The addition of 40 μL plasma sample starts the reaction. The components are incubated at 37° C.

The thrombin-substrate is cleaved by the generated thrombin and a fluorophore-containing moiety is released. The increase of the fluorescence intensity, which is proportional to the concentration of the generated thrombin, is monitored continuously at 37° C. by automatic reading every minute up to 120 min using a Microplate Fluorescence Reader FL600 (Bio-TEK Instruments, Winooski, Vt., USA) with an excitation wavelength of 360 nm and an emission wavelength of 460 nm.

The rate of development of fluorescence intensity [fluorescence units (FU)] is calculated for each reading (FU/min), and converted to thrombin-equivalent concentrations (nM) using a reference curve prepared by measuring the rate of substrate conversion by a purified thrombin added instead of the plasma sample.

The triggering effects of the frozen and lyophilized TF/PL-complexes (containing 18 pM TF and 3.2 μM PL) are compared by using a normal human plasma (FACT, George King Bio-Medical Inc. Overland Parks, Kans., USA) a FVIII inhibitor plasma without and reconstituted with 0.5 U/mL FEIBA (both products from Baxter, Vienna, Austria).

Figure 2:
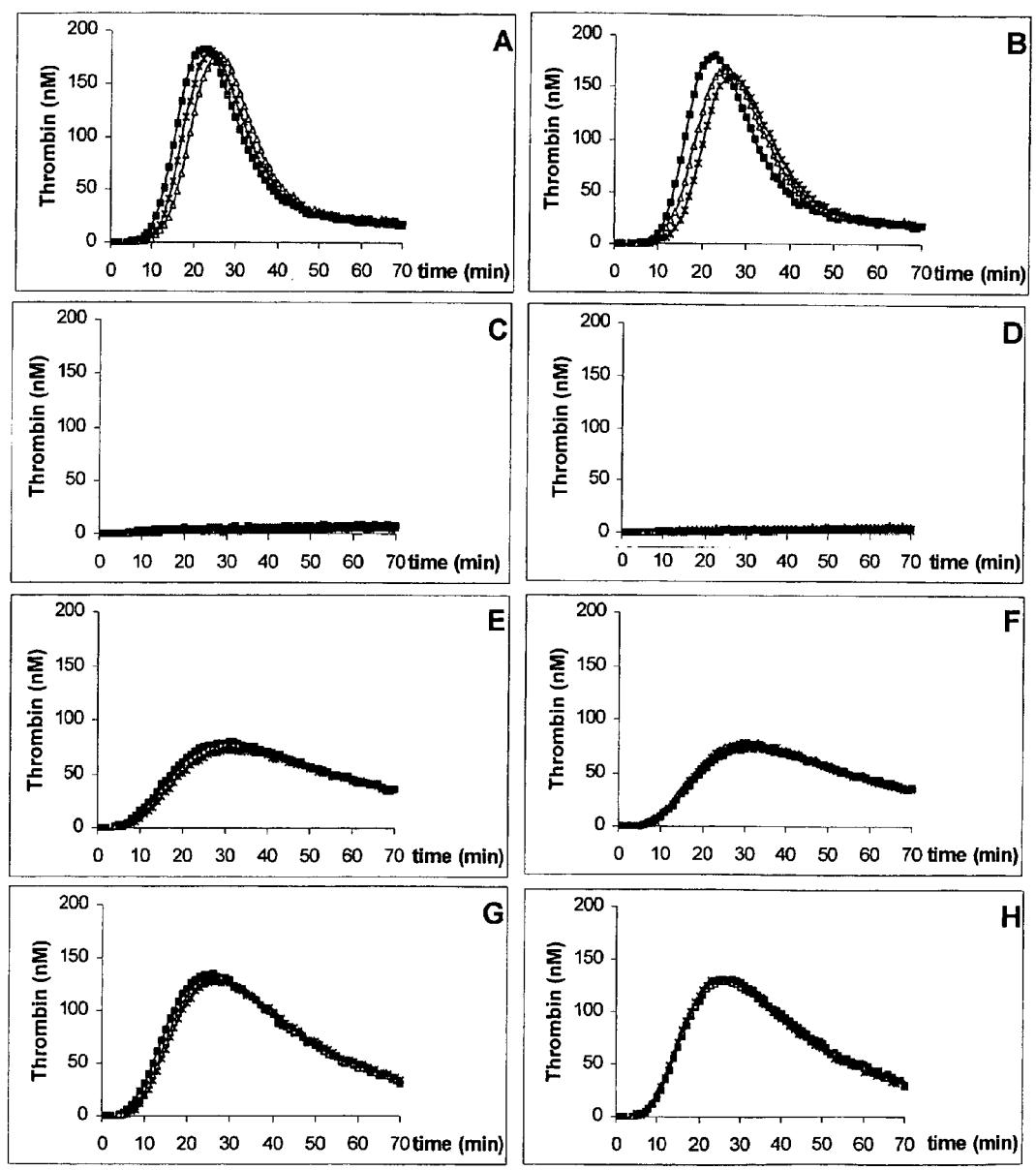
FIG. 2 shows thrombin generation curves triggered with frozen or lyophilized TF/PL-complexes in various plasma samples. It is demonstrated that there is no difference in the thrombin generation (shown as a curve of the thrombin concentration versus time) between the frozen and the lyophilized TF/PL-complexes. There is also no difference in the thrombin generation whether the TF/PL-complexes are lyophilized in the absence or presence of sucrose (used as a stabilizer). (A) Normal human plasma with frozen TF/PL-complex. (B) Normal human plasma with lyophilized TF/PL-complex. (C) FVIII inhibitor plasma with frozen TF/PL-complex. (D) FVIII inhibitor plasma with lyophilized TF/PL-complex. (E) FVIII inhibitor plasma reconstituted with 0.5 U/mL FEIBA with frozen TF/PL-complex. (F) FVIII inhibitor plasma reconstituted with 0.5 U/mL FEIBA with lyophilized TF/PL-complex. (G) FVIII inhibitor plasma reconstituted with 1 U/mL FEIBA with frozen TF/PL-complex. (H) FVIII inhibitor plasma reconstituted with 1 U/mL FEIBA with lyophilized TF/PL-complex. The symbols show: —■—without sucrose; —Δ—with 0.5% sucrose; —*—with 5% sucrose.

The thrombin generation curves are shown in FIG. 2.

Example 3

Comparison of the Thrombin Generation Triggering Effect of Frozen and Lyophilized TF/PL-Complexes with Various Compositions The TF/PL-complexes are prepared as described in Example 1, but composed of various phospholipids in a concentration of 3.2 μM with 18 pM or 89 pM TF. The TF/PL-complexes are frozen in aliquots or lyophilized without sucrose with the lyophilization cycle described in Example 1.

TABLE 2

Composition of TF/PL-complexes

| PL composition (weight ratio) | | PL concentration (μM) | TF concentration (pM) |
|---|---|---|---|
| PC:PS | 80/20 | 3.2 | 18 |
| PC:PS | 60/40 | 3.2 | 18 |
| PC:PS | 95/5 | 3.2 | 18 |
| PC:PS:PE | 78/17/5 | 3.2 | 18 |
| PC:PS:PE | 60/20/20 | 3.2 | 18 |
| PC:PS | 80/20 | 3.2 | 89 |
| PC:PS | 60/40 | 3.2 | 89 |
| PC:PS | 95/5 | 3.2 | 89 |
| PC:PS:PE | 78/17/5 | 3.2 | 89 |
| PC:PS:PE | 60/20/20 | 3.2 | 89 |

PC: 1,2-Dioleoyl-sn-glycero-3-phosphocholine (DOPC)
PS: 1-Palmitoyl-2-oleoyl-sn-glycero-3-phosphoserine (POPS)
PE: 1,2-Dioleoyl-sn-glycero-3-phosphoethanolamine (DOPE)

Figure 3:
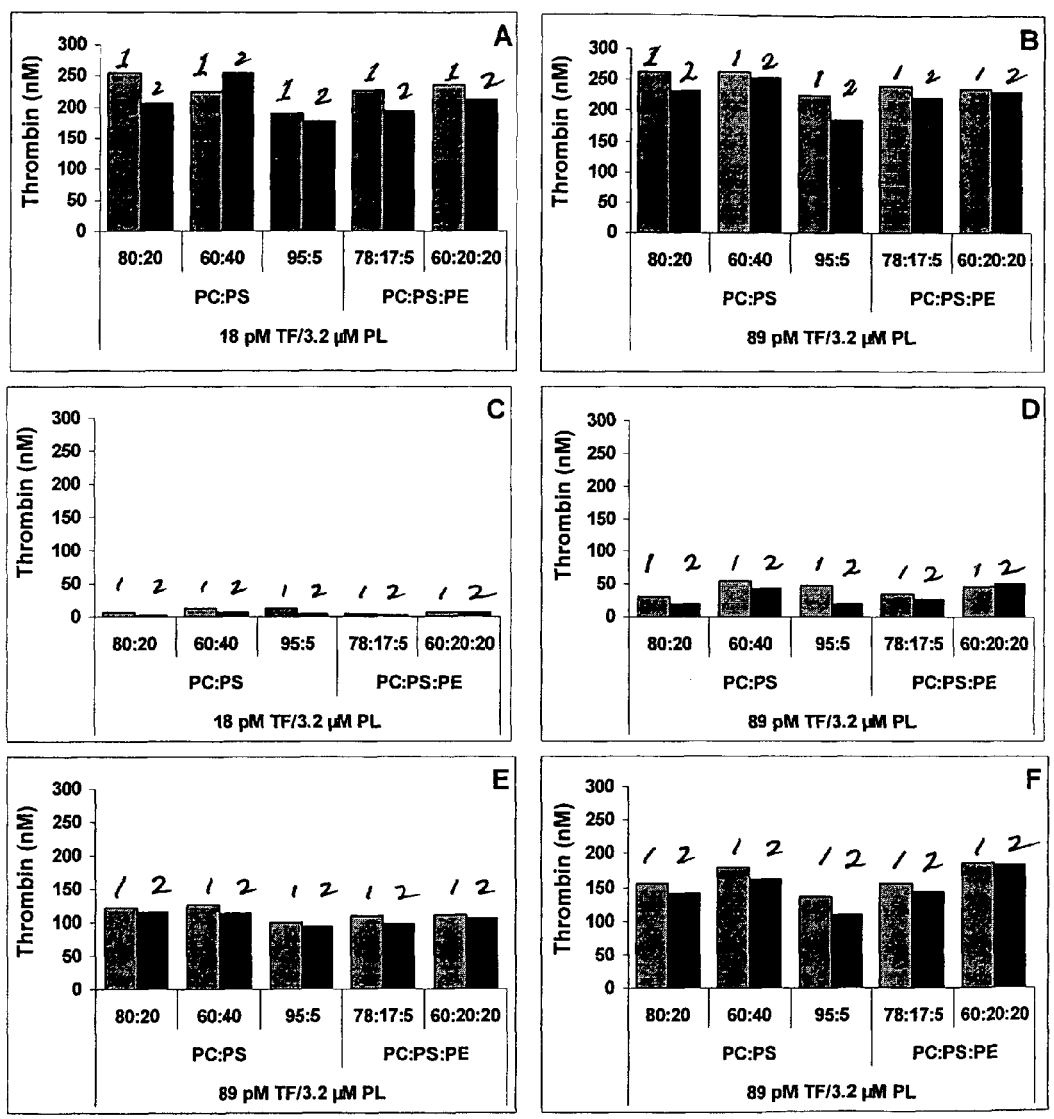
FIG. 3 shows the comparison of the peak thrombin, which is the highest thrombin concentration observed during the time course of formation and inactivation of thrombin, measured in normal human plasma and in FVIII inhibitor plasma, without FEIBA and reconstituted with 0.5 U/mL FEIBA, after triggered with frozen or lyophilized TF/PL-complexes of various compositions. (A) Normal human plasma with TF/PL-complexes containing low amounts of TF. (B) Normal human plasma with TF/PL-complexes containing high amounts of TF. (C) FVIII inhibitor plasma with TF/PL-complexes containing low amounts of TF. (D) FVIII inhibitor plasma with TF/PL-complexes containing high amounts of TF. (E) FVIII inhibitor plasma reconstituted with 0.5 U/mL FEIBA with TF/PL-complexes containing low amounts of TF. (F) FVIII inhibitor plasma reconstituted with 0.5 U/mL FEIBA with TF/PL-complexes containing high amounts of TF. The symbols show: —1—frozen reagents; —2—lyophilized reagents.

Thrombin generation curves are measured as described above. The most characteristic parameter, the peak thrombin, i.e. the maximum thrombin concentration measured during the time course of thrombin formation and inactivation, is calculated and drawn as a function of the TF/PL-complexes. FIG. 3 shows the peak thrombin concentrations measured in normal human plasma, in FVIII inhibitor plasma without and reconstituted with 0.5 U/mL FEIBA after triggered with the frozen or lyophilized TF/PL-complexes.

There was no difference in any of the plasma samples investigated whether thrombin generation has been triggered with the frozen or with the lyophilized TF/PL-complexes.

Example 4

Figure 4:
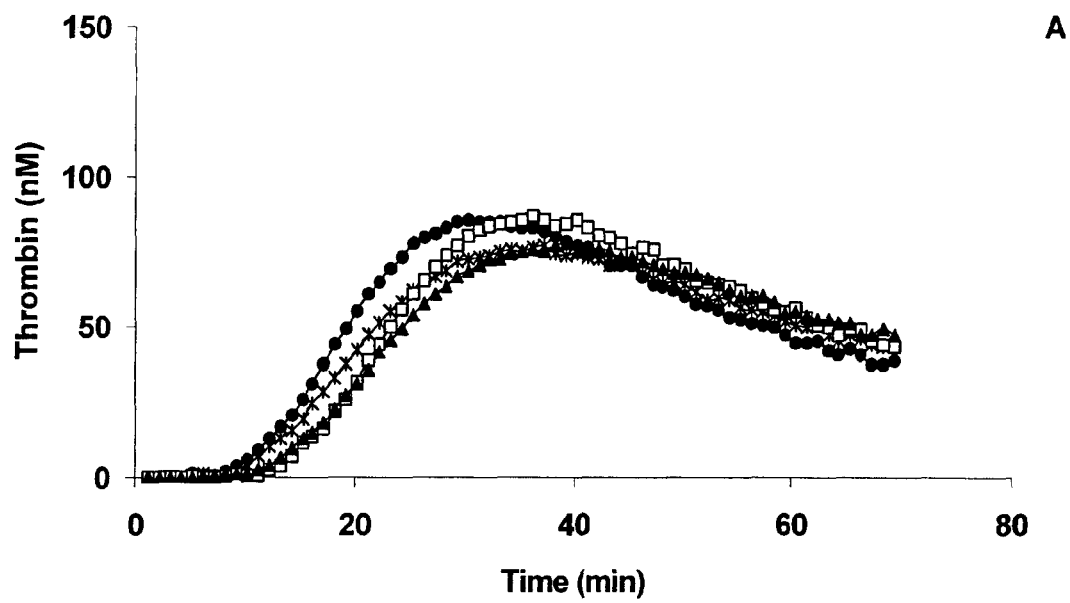
FIG. 4 shows that there is no difference in the obtained thrombin generation curves and peak thrombin concentrations obtained from these curves, whether the TF/PL-complex and the mixture containing a thrombin-substrate and $CaCl_2$ are lyophilized in a well of a microtiter plate individually or jointly. (A) Comparison of thrombin generation curves obtained in FVIII inhibitor plasma reconstituted with 0.5 U/mL FEIBA triggered with lyophilized TF/PL-complexes and measured with lyophilized mixtures containing a thrombin-substrate and $CaCl_2$ (—●—), triggered with TF/PL-complexes lyophilized in a well of a microtiter plate and measured with lyophilized mixtures containing a thrombin-substrate and $CaCl_2$ (—*—), triggered with lyophilized TF/PL-complexes and measured with mixtures containing a thrombin-substrate and $CaCl_2$ lyophilized in a well of a microtiter plate, (—□—) and triggered TF/PL-complexes and measured with mixtures containing a thrombin-substrate and $CaCl_2$ both lyophilized in a well of a microtiter plate (—▲—). (B) Comparison of the peak thrombin concentrations derived from panel A measured in normal human plasma, in FVIII inhibitor plasma without and reconstituted with 0.5 U/mL and with 1 U/mL FEIBA triggered with reagents lyophilized individually or jointly in a well of a microtiter plate. The symbols show: –1—triggered with lyophilized TF/PL-complexes and measured with lyophilized mixtures containing a thrombin-substrate and $CaCl_2$; —2—triggered with TF/PL-complexes lyophilized in a well of a microtiter plate and measured with lyophilized mixtures containing a thrombin-substrate and $CaCl_2$; —3—triggered with lyophilized TF/PL-complexes and measured with mixtures containing a thrombin-substrate and $CaCl_2$ lyophilized in a well of a microtiter plate; —4—triggered TF/PL-complexes and measured with mixtures containing a thrombin-substrate and $CaCl_2$ both lyophilized in a well of a microtiter plate.
Figure 4:
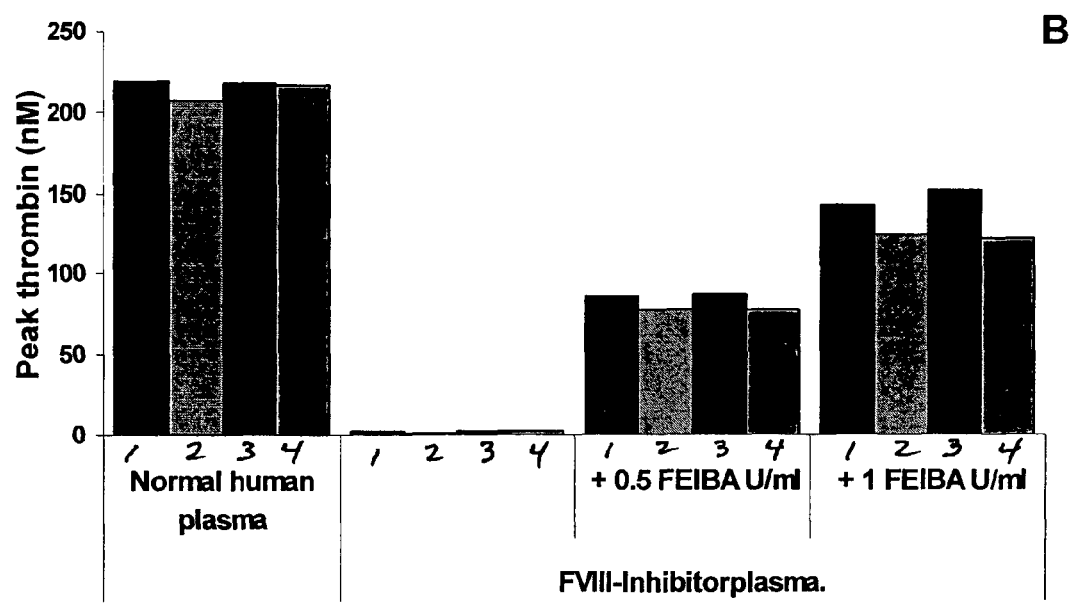

Lyophilization of TF/PL-complexes and Mixtures Containing a Thrombin-Substrate and $CaCl_2$ in the Wells of Microtiter Plates The thrombin generation assay is carried out in the wells of microtiter plates. Therefore, the TF/PL-complex and/or the mixture containing the thrombin-substrate and $CaCl_2$ are directly lyophilized individually or jointly on the wells of microtiter plates. When the two components are lyophilized jointly in a well of a microtiter plate, only the plasma sample to be tested have to be added in such a ready-to-use embodiment. FIG. 4 shows that there is no difference in the obtained thrombin generation curves and peak thrombin concentrations whether the TF/PL-complex and the mixture containing a thrombin-substrate and $CaCl_2$ are lyophilized individually or jointly in the well of a microtiter plate.

Example 5

Sensitivity of the Thrombin Generation Assay

Figure 5:
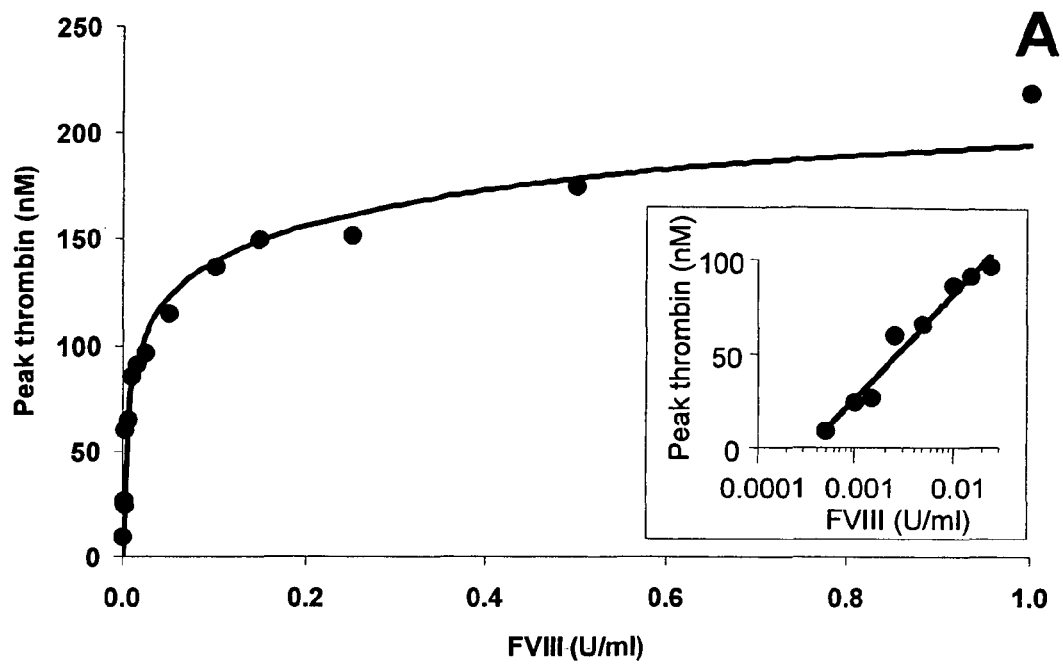
FIG. 5 shows the sensitivity of the thrombin generation assay to the FVIII and IX activities. (A) Factor VIII activity-dependent changes of peak thrombin. The enlarged section of this figure shows the values in the FVIII activities below 0.1 U/mL. (B) Factor IX activity-dependent changes of peak thrombin. The enlarged section of this figure shows the values in the FIX activities below 0.1 U/mL.
Figure 5:
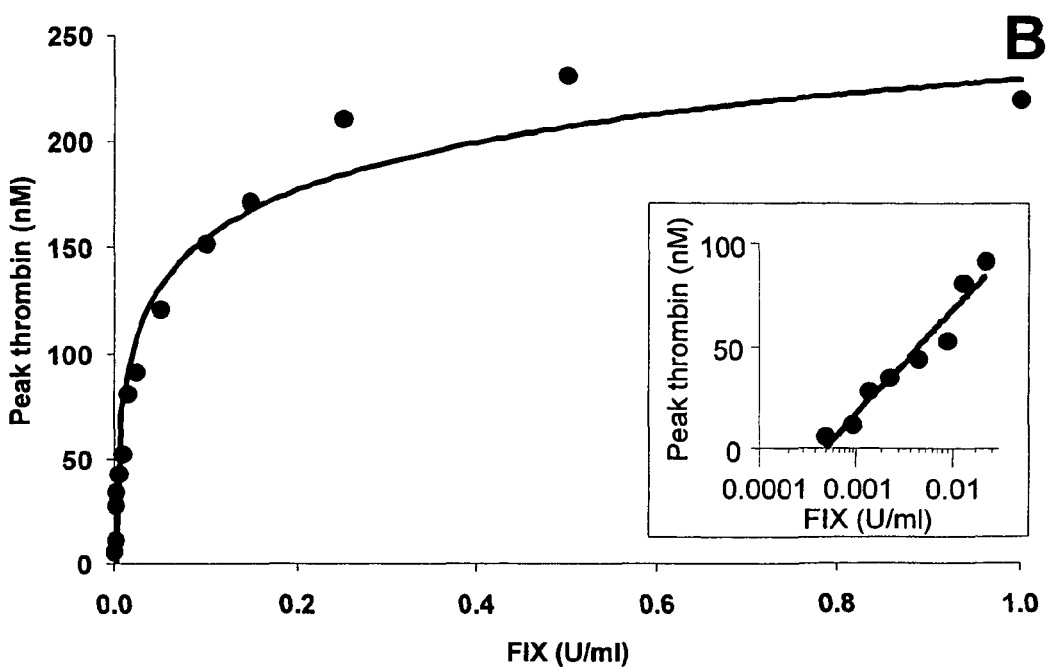

The thrombin generation assay is very sensitive to any coagulation factors alone or in groups. Therefore the assay can also be used to determine the efficacy of a substitution therapy as well as complex therapy with e.g. FVIII-bypassing agents. As it is seen in FIG. 5, the assay is especially sensitive in a low activity range, even below 0.01 U/mL of coagulation factors, which is the general detection limit of the usual clotting and chromogenic assays. Since there are differences in the bleeding tendency among the severe haemophiliacs, i.e. patients with a FVIII or FIX activity below 0.01 U/mL, the possibility of measuring the factor activities in this low range helps to avoid the spontaneous bleeding risk of these patients.

Example 6

Preparation of a Frozen and a Lyophilized Water-Soluble Mixture Containing a Thrombin-Substrate and $CaCl_2$ The Z-Gly-Gly-Arg-AMC/HCl thrombin-substrate is dissolved in 25 mM HEPES buffer pH 7.35 containing 175 mM NaCl and 10% of DMSO by magnetic stirring for 5 minutes, followed by the addition of $CaCl_2$. At this time a precipitate appears, which can be dissolved by vigorous shaking for 15 minutes at 37° C., followed by one hour slow stirring at room temperature. The resulting clear solution is composed of a final concentration of 5 mM thrombin-substrate and 75 mM $CaCl_2$. The solution is further diluted with HEPES buffer pH 7.35 containing 175 mM NaCl (without DMSO) to a final concentration of 1 mM thrombin-substrate and 15 mM $CaCl_2$, frozen in aliquots or lyophilized to give a "ready to use" solution after dissolving in water for injection. Also the concentrated solution (i.e. the solution containing 5 mM thrombin-substrate and 75 mM $CaCl_2$) can be frozen in aliquots or lyophilized and optionally diluted to an appropriate concentration before use.

We claim:

1. A method for measuring the thrombin generation in whole blood or plasma, comprising the steps of:
   (a) providing a lyophilized tissue factor (TF)/phospholipid (PL)-complex and a lyophilized mixture that is dissolvable in water and contains a thrombin-substrate comprising a fluorescent label and $CaCl_2$;
   (b) mixing said lyophilized TF/PL-complex and said lyophilized mixture containing thrombin-substrate and $CaCl_2$ in an amount of plasma or whole blood sample that provides a concentration of 1 mM thrombin substrate and 15 mM $CaCl_2$, wherein the lyophilized TF/PL-complex and the lyophilized mixture containing the thrombin-substrate and $CaCl_2$ are immobilized on a solid support; and
   (c) measuring the thrombin generation in said sample.

2. The method according to claim 1, wherein the sample is a cell-free plasma sample.

3. The method of claim 1, wherein the thrombin substrate is Z-Gly-Gly-Arg-AMC.

4. The method of claim 1, wherein the concentration of TF in the lyophilized TF/PL-complex ranges from about 5 to about 1000 pM.

5. The method of claim 1, wherein the concentration of PL in the lyophilized TF/PL-complex ranges from about 1 to about 100 μM.

6. The method of claim 1, wherein the TF is of recombinant origin.

7. The method of claim 1, wherein the PL is a mixture comprising phosphatidylserine (PS) and phosphatidylcholine (PC); or a mixture comprising PS, PC, and phosphatidylethanolamine (PE).

8. The method of claim 1, wherein the PL is a mixture of PS and PC, and the weight ratio of PC/PS is in the range of from about 60/40 to about 95/5 based on the total amount of phospholipid.

9. The method of claim 1, wherein the PL is a mixture of PS, PC, and PE, and the weight ratio of PC/PS/PE is in the range of from about 60/20/20 to about 78/17/5, based on the total amount of phospholipids.

10. The method of claim 1, wherein the solid support is the inner surface of a well of a microtiter plate.

\* \* \* \* \*